United States Patent [19]
Owsley

[11] Patent Number: 5,727,561
[45] Date of Patent: Mar. 17, 1998

[54] METHOD AND APPARATUS FOR NON-INVASIVE DETECTION AND ANALYSIS OF TURBULENT FLOW IN A PATIENT'S BLOOD VESSELS

[75] Inventor: Norman L. Owsley, Gales Ferry, Conn.

[73] Assignee: The United States of America as represented by the Department of the Navy, Washington, D.C.

[21] Appl. No.: 641,049

[22] Filed: Apr. 23, 1996

[51] Int. Cl.⁶ .................................................. A61B 5/026
[52] U.S. Cl. .................................. 128/691; 128/687
[58] Field of Search .......................... 128/672, 687–691

[56] References Cited

U.S. PATENT DOCUMENTS

5,140,991  8/1992  Niwa ........................................ 128/687
5,365,930  11/1994  Takashima et al. ...................... 128/687
5,617,869  4/1997  Austin et al. ............................. 128/672

*Primary Examiner*—William R. Kamm
*Assistant Examiner*—George R. Evanisko
*Attorney, Agent, or Firm*—Michael J. McGowan; James M. Kasischke; Prithvi C. Lall

[57] ABSTRACT

A method and apparatus for the diagnosis of pathological turbulent arterial blood flow in a patient includes energy wave detectors for sensing at a plurality of spaced positions on the patient forces generated by turbulent arterial blood flow. The detectors generate a plurality of space time signals that are arranged in a vectorized data structure. A processor converts the vectorized data structures into an output that indicates the form of the waves propagated from the site of the turbulent arterial blood flow, the location and spatial configuration of that site.

21 Claims, 6 Drawing Sheets

METHOD AND APPARATUS FOR NON-INVASIVE DETECTION AND ANALYSIS OF TURBULENT FLOW IN A PATIENT'S BLOOD VESSELS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

(1) Field of the Invention

This invention generally relates to apparatus and methods for non-invasive analysis of flow in a tube and more particularly to an apparatus and method for non-invasive detection and analysis of turbulent blood flowing in blood vessels.

(2) Description of the Prior Art

It is well known that the turbulent blood flow in one or more vessels in an individual often indicates the presence of arterial diseases or defects. That is, the detection of turbulent blood flow within a patient's blood vessels can serve as a primary diagnostic indicator of occlustic, aneurystic, thrombotic and other like vascular conditions.

The following United States Letters Patent disclose various methods and apparatus for detecting, measuring and/or analyzing cardiopulmonary and/or vascular conditions:

| | |
|---|---|
| 5,337,752 (1994) | Reeves |
| 5,309,992 (1994) | Schechter et al. |
| 5,109,863 (1992) | Semmlow et al. |
| 5,012,815 (1991) | Bennett, Jr. et al. |
| 5,010,889 (1991) | Bredesen et al. |
| 4,792,145 (1988) | Eisenberg et al. |
| 4,720,866 (1988) | Elias et al. |
| 4,568,514 (1986) | Schlager et al. |

U.S. Pat. No. 5,337,752 to Reeves discloses a system that matches an acoustic blood flow signal and electro-cardiogram patterns of heart sound to detect, assess and diagnose a variety of valvular and arrythmia conditions. The acoustic blood flow signal is generated by a microphone or transducer positioned on the patient's body while the electro-cardiogram is produced by standard electro-cardiographical devices and is used to generate a systolic cycle based timing signal. The timing signal is used to produce a spectral pattern from the blood flow signal.

U.S. Pat. No. 5,309,992 to Schechter et al. discloses a respiratory sound analyzer for use in noisy environments. The disclosed analyzer includes two arrays of two or more accelerometers each defining a transducer which are preferably spaced on the patient's chest to sense the vibration caused by breathing action. An additional accelerometer array may be placed on another portion of the patient to generate a noise signal to be subtracted from the signals detected by the first two arrays. The analyzer digitizes and stores by time the signals detected by the two sensors and then processes the stored signals by Fourier analysis, time comparisons or the like to ascertain problems and/or changes in the breathing pattern of the patient.

U.S. Pat. No. 5,012,815 to Bennett, Jr. et al. discloses a system for generating a spectral phonocardiogram that summarily indicates time dependent changes in sound generated by the heart during heart cycling. The system includes two microphones disposed on a patient's chest. The system processes the detected signals in parallel by amplification, analog filtering and digitization to provide a series of 1,024 stored data points that are then multiplied by a 1,024 point time window function that has zero slope and amplitude at the start and end of the window. The resultant serial streams of data are then Fourier transformed to provide a frequency-time-amplitude spectral image data for analysis of the sensed signals.

U.S. Pat. No. 5,010,889 to Bredesen et al. discloses a stethoscope that automatically diagnoses abnormalities of a patient and enables single point auscultation of the patient. The stethoscope includes a recorder for recording body sounds from various locations of a patient's body obtained by sequentially moving a conventional stethoscope bell to the various locations. The received signals are digitized and characterized according to specified characteristics to define a matrix of signal characteristics. This matrix is then compared with stored matrices to identify commonality between one or more of the stored matrices that conform to known abnormalities of the heart, lungs or other bruits.

U.S. Pat. No. 5,109,863 to Semmlow et al. discloses an apparatus for analyzing diastolic heart sounds to identify turbulent blood flow in partially occluded arteries. The apparatus includes an acoustic transducer coupled to a patient's chest to generate a heart signal, a pulse detector to provide a timing reference signal, and a processor for the heart and pulse signals. The processor provides a diastolic frequency spectrum and diagnostic information display based upon parametric modeling and averaging. The processing units may include parametric noise modeling techniques such as autoregressive, autoregressive moving average and eigenvector based methods to detect and classify turbulent flow associated with osculated coronary arteries.

U.S. Pat. No. 4,792,145 to Eisenberg et al. discloses a microprocessor based sound enhancement system that converts acoustic vibrations from a patient to electrical signals including frequencies and intensities not ordinarily within the auditory range of a physician. The system includes a microphone connected to a wide band amplifier. The amplified sounds are preferably time-gated at a rate corresponding to the duration and separation of the patient's heart beats. The system digitizes and compresses the detected signals by short time Fourier transform analysis. A sound generator re-produces from the compressed signal sounds with the same tonal relationships as sensed but at a higher and audible frequency and level.

U.S. Pat. No. 4,720,866 to Elias et al. discloses a device that identifies medical conditions from amplified and filtered stethoscopic data. A band pass filter couples portions of the signal in a particular band width to level detectors that produce an output signal with a root mean square value of the average input over a time period corresponding to the time constant of the level detector. The output signals are selectively digitized and accumulated for selective transmission to a graphic display depicting sound intensity (signal amplitude) versus frequency of the signal and time for auscultation analysis.

U.S. Pat. No. 4,586,514 to Schlager et al. discloses a non-invasive instrument for detecting arterial restrictions. The instrument includes a microphone positioned on a patient's body to generate a signal that is then filtered, amplified, digitized and separated into discrete frequency bins. Each of the signals are then converted by a band pass filter including an AC (RMS) to DC (average) converter to provide a DC output signal used to produce a graphic display.

The foregoing references disclose methods and apparatus for non-invasive monitoring of the sounds generated within a patient's body to diagnose and treat the patient. They all however fail to provide a relatively low cost, easy to use, and efficient multi-channel system for detecting space time signals to locate and diagnose artery disease.

SUMMARY OF THE INVENTION

It is therefore an object of this invention to provide a method and apparatus for non-invasively detecting turbulent flow in a blood vessel.

It is another object of this invention to provide a method and apparatus for processing a plurality of space time signals to generate a frequency time spectral analysis of the space time signals.

It is still another object of this invention to provide a relatively low cost, effective and simple apparatus for generating space time signals corresponding to sensed turbulent flow in a patient and for processing the signals to locate the turbulent flow.

It is yet another object of this invention to provide a method and apparatus for producing an autopower spectrum analysis of space time signals at each volumetric point selected in a patient.

According to one aspect of this invention an apparatus for the diagnosis of pathological turbulent arterial blood flow in a patient includes a plurality of spaced shear wave front sensors that generate a plurality of space time signals responsive to arrival of propagated forces from a site of turbulent arterial blood flow. Interfacing circuitry generates a vectorized data structure in response to the space time signals from the multiple wave front sensors and a digital signal processor generates a report signal indicating the location and spatial extent of the turbulent arterial flow and the wave form propagating from the site of the turbulent flow.

According to another aspect of this invention a method for providing diagnostic information with respect to turbulent arterial blood flow in a patient includes the steps of sensing at a plurality of spaced locations vibrational force shear waves generated by the turbulent flow and generating corresponding data vector structures corresponding to the force waves sensed at selected time intervals. Processing the data structure produces an imaging signal corresponding to the tissue through which the force waves pass to indicate the nature and location of the turbulent flow.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE PREFERRED EMBODIMENT

Figure 1:
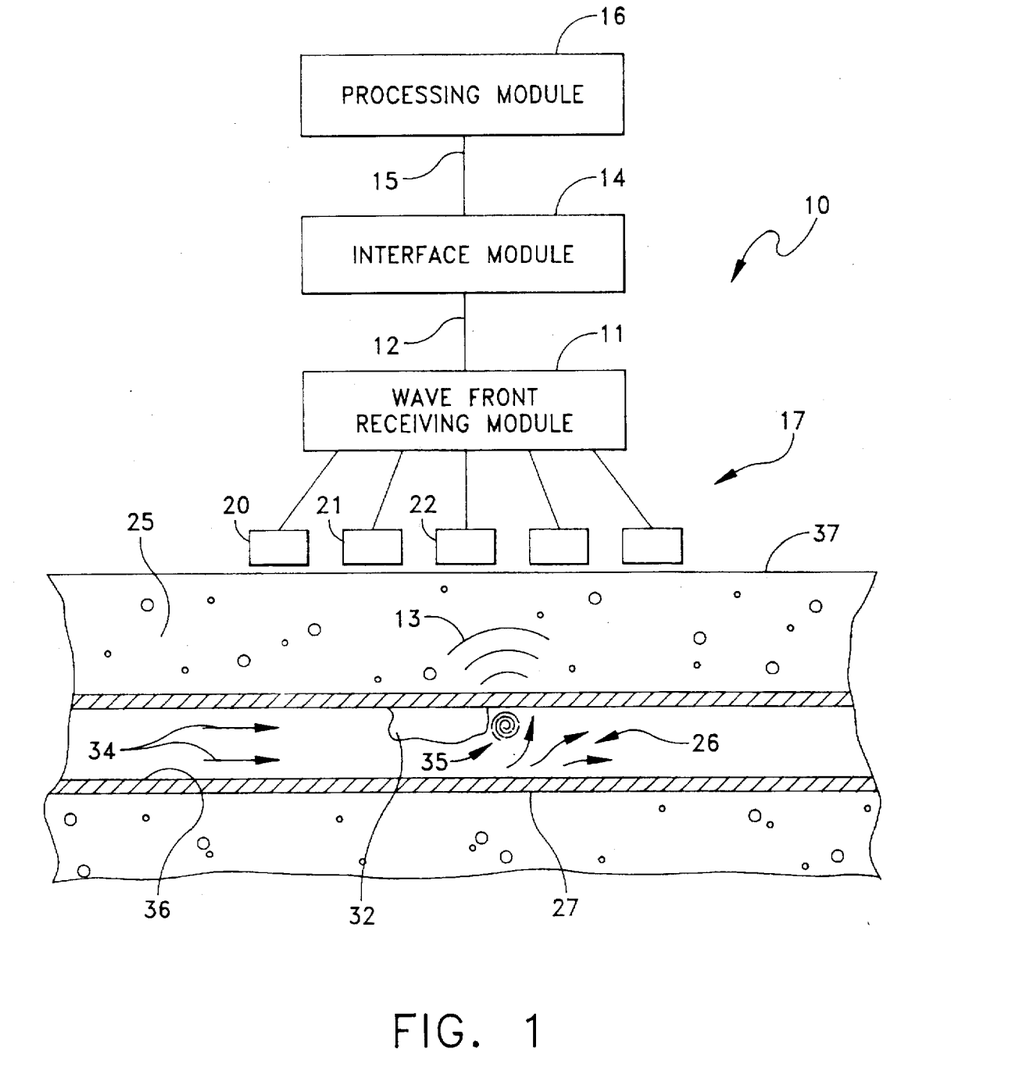
FIG. 1 is a schematic diagram including apparatus for detection and analysis of turbulent blood flow embodying this invention.

An embodiment of an apparatus 10 according to this invention for detecting, locating and analyzing turbulent flow as depicted in FIG. 1 includes a wave front receiving module 11 that generates electrical signals 12 corresponding to vibrational force waves 13 and transmits the signal 12 to an interface module 14. The interface module 14 in turn directs output signals comprising vectorized data structures 15 to a processing module 16.

The vibrational wave receiving module 11 comprises an array 17 of a plurality of spaced strain measurement detectors, such as detectors 20, 21 and 22 for receiving waves 13 transmitted through the patient's tissue 25 in response to blood turbulence and generate electrical signals 12 corresponding to the amplitude and frequency of those waves 13. The interface and processing modules 14 and 16 include various elements that filter, condition, process and analyze the signals 12 generated by the wave receiving processor 11 corresponding to the vibrational waves 13 incident at the detector array 17. These elements, as further explained below, enable a user to identify the existence of turbulent flow 26 in a vessel 27, to locate the position of the turbulent flow 26 relative to the detector array 17 and to determine the nature of the turbulent flow volume 26 thereby to enable a diagnosis of the abnormality in the vessel 27.

As seen in FIG. 1, the turbulent flow in the vessel 27 generates the waves 13 that travel through the non-homogeneous elastic medium of the body tissue 25. In this instance, the vessel 27 includes an arterial occlusion 32 of the type frequently resulting from a build up of plaque. The occlusion 32 transforms normal laminar blood flow indicated by the arrows 34 upstream of the occlusion 32 to a chaotic, turbulent flow 26 distally or downstream relative to the occlusion 32. This turbulence flow 26 contains eddies 35 which, in turn, cause time varying forces both tangential to and normal to the wall 36 defining the vessel 27. These forces result in the propagating waves 13 that can be described as signals which exist simultaneously in the three spatial dimensions and time.

The placement of the vibrational detectors of the detector array 17 on the surface of a patient's skin 37 enables simultaneous processing of the electrical signal 12 from the wave front receiving module 11 by the interface module 14 and the processing module 16 (1) to detect the existence of the turbulent blood flow 26; (2) to locate the position of the turbulent blood flow 26 relative to the array 17 by creating a propagating wave energy intensity image of the volume containing the turbulent blood flow; and (3) to enhance the fidelity (signal to background noise power ratio) of the signal which originates from the artery turbulent blood flow mechanism and thereby improve the quality of a subsequent analytic diagnosis of the arterial condition relative to the fidelity which could be obtained with either one or two such detectors.

The wave front receiving module 11 comprises an auscultatory sensing device for generating a plurality of signals from a plurality of spaced locations corresponding to the waves sensed at the locations. The wave front receiving module 11 includes the array 17 comprising the plurality of auscultatory sensors detectors (e.g., detectors 20, 21, 22) that exhibit a high sensitivity over a wide temporal frequency band (i.e., from 100 cycles per second to as high as 2000 cycles per second). The detectors defining the array 17 are arranged in a predetermined spaced relationship and generate a plurality of signals responsive to the incidence of waves 13 at their respective locations. The signals 12 generated by each of the detectors of the array 17 varies both in time and intensity due to the spacing of the detectors and the distance from the turbulent flow 26.

The spacing between some of the contiguous detectors of the array 17 should be equal to or less than:

$$D_{N(x,y,z)} - D_{N-1(x,y,z)} \leq \frac{C_W}{2f_{max}} \quad (1)$$

Figure 2:
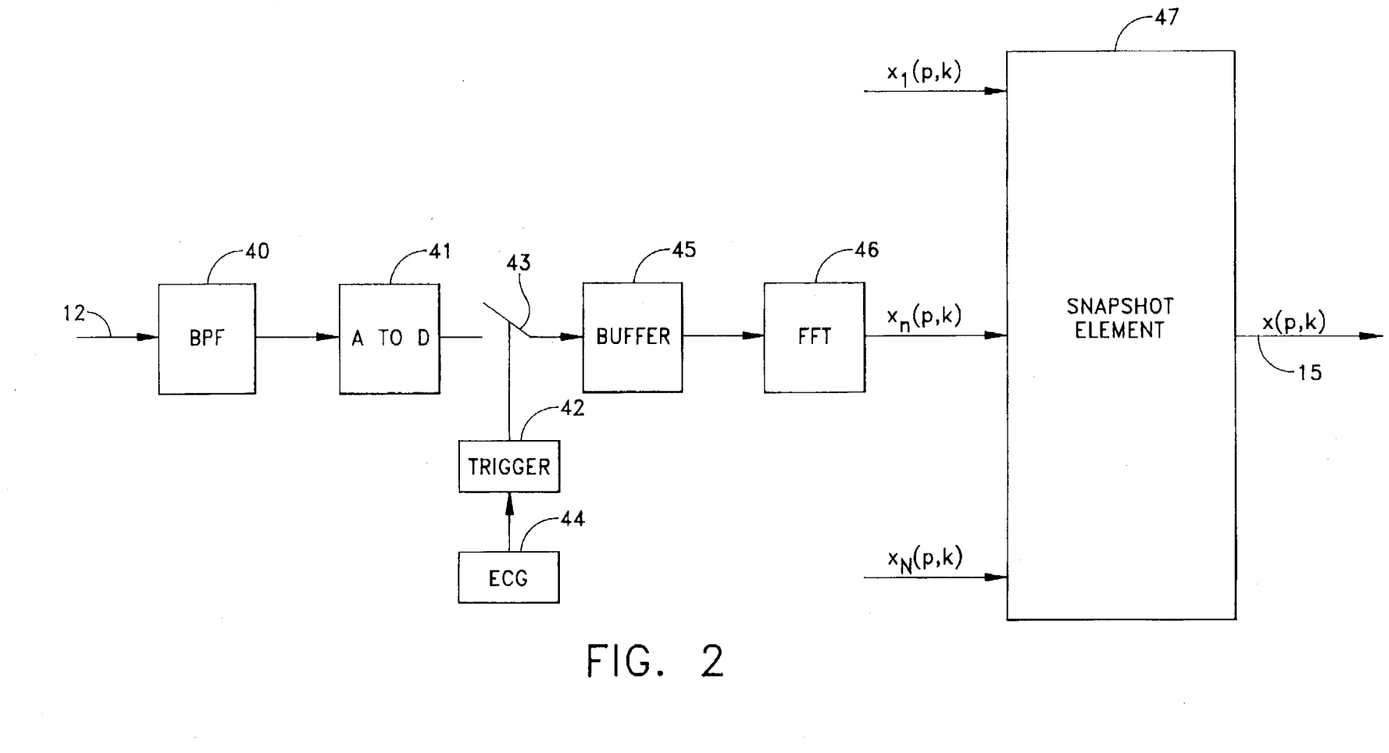
FIG. 2 is a block diagram of an interface module of the embodiment of FIG. 1.

The terms "$D_{N(x,y,z)}$" and "$D_{N-1(x,y,z)}$" designate the relative positions of the Nth and (N−1)th detectors of the plurality of the detectors comprising the array 17. The term "$C_w$" represents the maximum speed of the propagated waves 13 in the patient's tissue 15. The term "$f_{max}$" corresponds to the highest frequency remaining in the signal after filtering, that is, the upper frequency of a band pass filter 40 (FIG. 2). This limitation ensures some time overlap in the signals received at such detectors.

The maximum separations of each of two adjacent detectors in the array 17 along two orthogonal axes in the plane of the array define the detector array apertures. The magnitude of the aperture in each of the axial directions is inversely proportional to the spatial resolution that is achieved in the axial direction. The spacing and the accuracy of the placement of the detectors in the array 17 determines the level of ambiguity in an image produced by the processing module 16.

The number of detectors in the array 17 directly and proportionally affects the level of diagnostic accuracy in analyzing the temporal frequency spectrum (signature) and locating abnormality in a patient's vessel. The array 17 preferably is a conformal two-dimensional array that enhances background noise discrimination. Background noise tends to be canceled by the concurrent signals from a two-dimensional array received by subsequent processing in the interface module 14 and the processing module 16. However, a lineal array produces acceptable results if background noise is acceptable or a natural anatomic feature such as ribs attenuates such noise.

In locating the array 17 of the wave front receiving module 11 on an individual, the user preferably positions the array 17 to provide a relatively direct path that is free of internal inhomogeneities (e.g., bones) between the potential turbulence volume and the detector locations. Of course, the user upon initial analysis can reorient the array 17 to achieve this proximity to a detected turbulent flow. Alternatively the user may use a tomographic, X-ray, ultrasonic or other source image to account for such inhomogeneities in the detected signals, as described hereinafter.

The interface module 14 receives and retains in digital form and as separate signals, the signals 12 from each of the detectors of the array 17. The components of the interface module 14 as depicted in FIG. 2 include one band pass filter 40 for each detector that preferably can be adjusted by the user to control the upper and lower frequency cutoffs. An analog-to-digital (A/D) converter 41 converts each of the filtered signals to a digital form. Obviously, the band pass filter 40 can be a digital filter which is positioned after the analog-to-digital converter 41. A trigger 42 controls a gate 43 for gating the digitized signals in synchronism with a selected time interval during a cardiac cycle when blood flow rate is sufficiently high to induce the turbulent flow 26 in the vessel 27 as depicted in FIG. 1. Thus, the interval will generally be centered about the systole or diastole points of the cardiac cycle. An electrocardiogram device 44 provides an input to the trigger 42.

Figure 3:
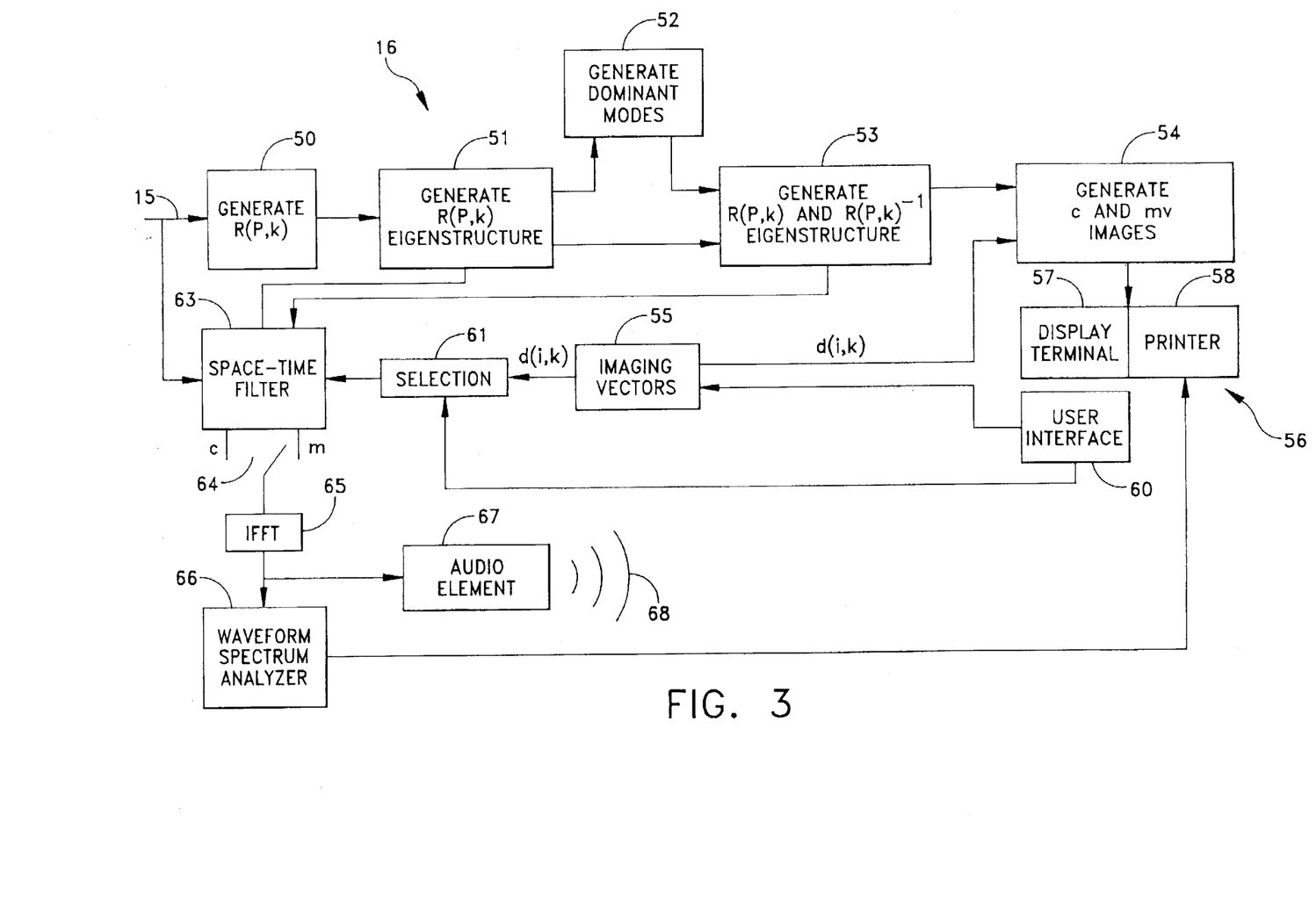
FIG. 3 is a block diagram of a processing module of the embodiment of FIG. 1.

A data buffer 45 receives and queues the digitized signals to form discrete overlapping time sample blocks of equal time duration. The amount of temporal overlap and the duration of each of the blocks are preferably preset in a known manner. A continuous sequence of either contiguous or identically overlapping blocks of the queued data in the data buffer 45 are then transformed by fast Fourier transformation in a transformation element 46 to produce a series of vectorized data structures 15 or "snapshots" in a holding element 47 for each time interval indexed by "p" and discrete frequency bin indexed by "k". The vectorized data structures as generated then can transfer to the processing module 16 (FIG. 3).

In the processing module 16 a generating element 50 that receives the vectorized data structure signals 15 from the interface module 14 of FIG. 1 and determines, for each discrete time interval and frequency bin, a cross-spectral density matrix (CSDM) "R(p,k)". Eigenstructure element 51 then computes an eigenstructure and eigenvectors of the cross-spectral density matrix so a dominant mode element 52 can determine the dominant propagating modes. A lower rank cross-spectral density matrix generating element 53 generates an approximatation of a low rank cross-spectral density matrix and its inverse. The lower rank cross-spectral density matrix and its inverse are passed to an image generating element 54 that also receives imaging vectors from an imaging vector element 55. The processing module 16 elements 50, 51, 52, 53 and 54 can be implemented on a general purpose computer through software. The imaging vector element 55 generates a conventional image and a minimum variance image that is transmitted to a reporting element 56 that includes a known sensory report generating device such as a display terminal 57 and/or a printer 58.

A user interface 60 enables a user to select particular imaging points and frequencies for generating a second report comprising or corresponding to an estimate of the space time waveform of the sensed signals 13 at selected points within the volume being imaged. The user selection causes the imaging vector element 55 to generate the imaging vector "$d(x_e, y_e, z_e, k)$" for the select frequency bin "k", where ($k_L \leq k \leq k_H$), and for the selected point "$x_e, y_e, z_e$". The selected point, imaging vector and frequency bin information signals are received by selection element 61 and directed to a space time filter element 63. The space time filter element 63 calculates conventional Fourier coefficients and minimum variance Fourier coefficients for the imaging points and produces the imaging vector that corresponds to the temporal spectrum of the turbulent blood flow induced energy wave form.

A switch 64, that is user selectable, transmits the conventional or minimum variance Fourier coefficients output of the filter element 63 to an inverse fast Fourier transform element 65 that performs the inverse fast Fourier transformation with zero padding and overlap to produce a time sampled turbulent flow wave form time series estimate. This wave form time series estimate is transferred to a spectrum analysis element 66 having an output normalized to the peak value in dB. The peak is preferably normalized at 0 dB and then reported by the reporting element 56. The output of the element 65 can also be reported by an audio system element 67 to produce an auditory signal 68 for analysis by the user.

Figure 4A:
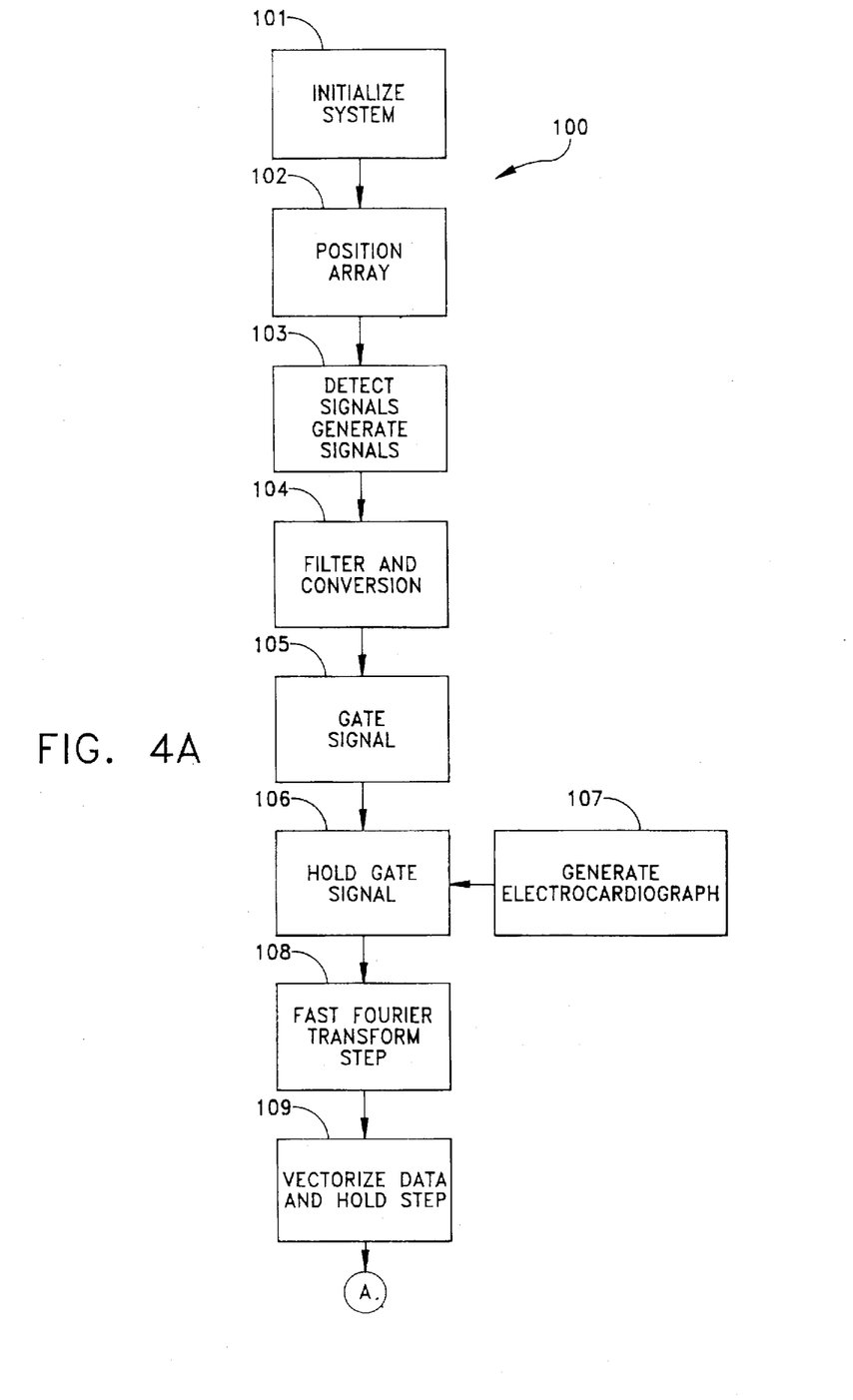
FIG. 4A, 4B and 4C is a flow chart of the embodiment of this invention.
Figure 4B:
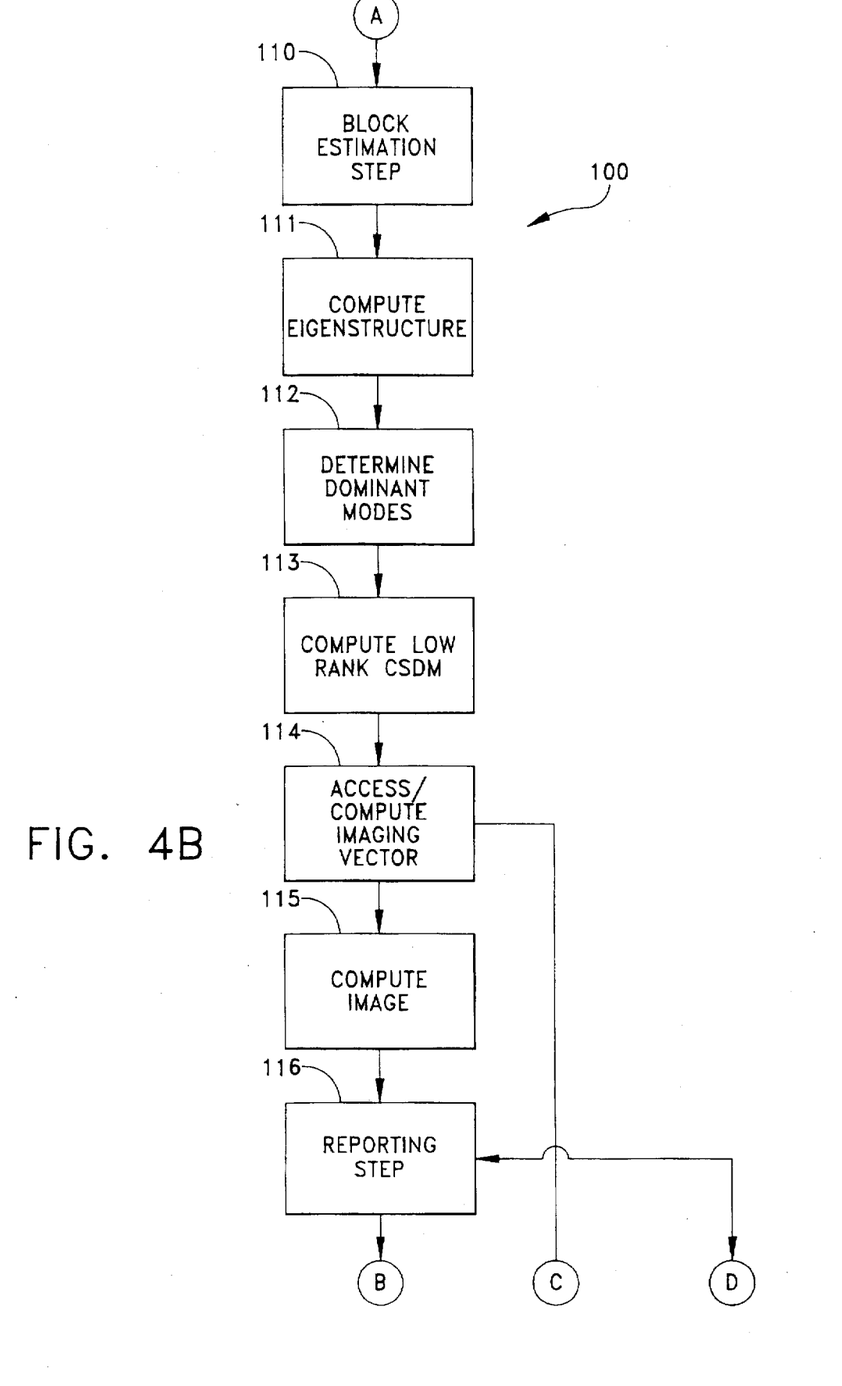
Figure 4C:
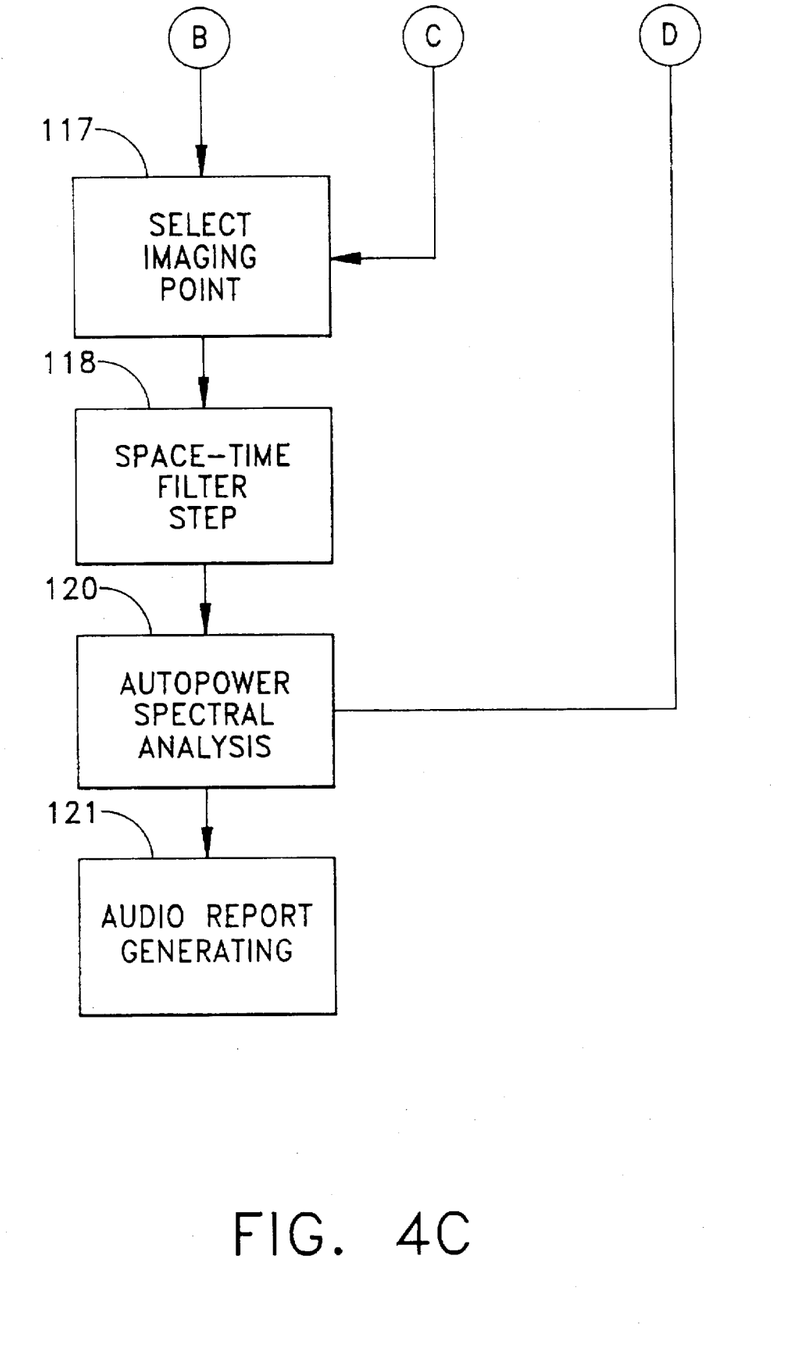

FIGS. 4A, 4B and 4C depicts a flow chart 100 indicating the operational sequence of the embodiment of FIG. 1 and includes system initialization in step 101 followed by positioning the sensor array in step 102. A detect and generate signals step 103 senses the wave at each detector in the array 17 positioned on the patient's body and generates corresponding analog signals. A filter and conversion step 104 filters the generated signals and passes a desired frequency range which is then converted to a digital signal. A gating step 105 passes the digital signals according to a selected time interval. Preferably the time interval selected corresponds to the cardiac cycle of the patient during which blood flow is sufficiently high to generate a turbulent flow to a holding step 106. A generate electro-cardiographic signal step 107 provides the interval to control the gating step 105. The holding step 106 arranges or accumulates the time sample signals from each of the detectors into a sequence of data in a buffer memory representing overlapping discrete time sampled blocks of equal time duration. The initialization step 101 provides the length of the interval duration and the temporal overlap of these blocks.

FIGS. 4A through 4C depict the steps by which the system in FIG. 3 connects the signals in the buffer 45 into an output that provides diagnostic information. In step 108 the FFT element performs a Fast Fourier Transform (FFT) of a continuous sequence of contiguous or identically overlapping blocks of the data. In step 109 the element 47 places the FFT data into a vectorized data structure defined as a N-by-1 complex vector "x(p,k)", referenced as a frequency-time sampled "snapshot" and specified as:

$$x(p,k) = \begin{bmatrix} x_1(p,k) \\ x_2(p,k) \\ \cdot \\ \cdot \\ \cdot \\ x_N(p,k) \end{bmatrix} \quad (2)$$

wherein "N" represents the total number of sensors in the array 17 and "p" is the snapshot time interval index and "k" is a discrete frequency index with $$\left(t_p - \frac{T}{2}\right) \le t < \left(t_p + \frac{T}{2}\right) \text{ for } (p = 0,1 \ldots P-1) \quad (3)$$

and where $$t_p = \frac{pT}{Q} \quad (4)$$

with "Q" representing the FFT interval overlap factor and "k" representing the discrete frequency index given by:

$$f_k = \frac{k}{T} \text{ for } (k = k_L, k_L + 1, \ldots, k_H) \quad (5)$$

The terms "$k_L$" and "$k_H$" represent the low and high cutoff frequencies for the band pass filter that the user preferably selects during the initialization step 101.

Referring now to FIG. 4B, step 110 then provides a block estimation "R(P,K)" of the cross spectral density matrix for each of the snapshot vectors as generated at each discrete frequency index k by the following equation:

$$R(P,k) = \frac{1}{P} \sum_{P=0}^{P-1} x(p,k) \, x(p,k)^H \quad (6)$$

where "P" is from one to three times as large as the number of detectors in the array 14 and the "H" is the matrix complex conjugate transpose operator. Step 111 then produces the eigenstructure of R(P,k) in ranked order from largest to smallest eigenvalues "$\lambda_1(P,k)$, $\lambda_2(P,k)$, . . . , $\lambda_N(P,k)$" and corresponding eigenvectors "$m_1$ (p,k), $m_2$ (p,k), . . . , $m_N(p,k)$". The $N_s$ eigenvalues that are larger than an average estimated background noise value are determined by step 112 to be the dominant propagating modes by the following:

$$\hat{o}(P,k)^2 = \frac{1}{N-N_S} \sum_{n=(N-N_S)+1}^{N} \lambda_m(P,k) \quad (7)$$

-continued $$\hat{o}(P,k)^2 = \frac{1}{N-N_S}\left(\text{Trace}[R(P,k)] - \sum_{n=1}^{n_S} \lambda_m(P,k)\right)$$

Step 113 computes a low rank CSDM approximation of R(p,k) and its inverse by the following respective equations:

$$\hat{R}(P,k) = e \sum_{n=1}^{N_S} (\lambda_m(P,k) - \hat{o}(P,k)^2) m_m(p,k) m_m(p,k)^H + \hat{o}(P,k)^2 I_N \quad (8)$$

and with e=1

$$\hat{R}(P,k)^{-1} = \quad (9)$$

$$\frac{1}{\hat{o}(P,k)^2}\left[I_N - \sum_{n=1}^{N_S}\left(\frac{\lambda_m(P,k) - \hat{o}(P,k)^2}{\lambda_m(P,k)}\right) m_m(p,k) m_m(p,k)^H\right]$$

The term "e" is a selectable scaling factor and the term "$I_N$" is an N-by-N identity matrix. Step 114 then computes or accesses a pre-computed imaging vector for the patient given generally by:

$$d(x_i,y_i,z_i,k) = \alpha(i,k) \begin{bmatrix} \frac{1}{d_i(1)^\beta} \exp\left(\frac{-j\omega_k d_i(1)}{c}\right) \\ \frac{1}{d_i(2)^\beta} \exp\left(\frac{-j\omega_k d_i(2)}{c}\right) \\ \cdot \\ \cdot \\ \cdot \\ \frac{1}{d_i(N)^\beta} \exp\left(\frac{-j\omega_k d_i(N)}{c}\right) \end{bmatrix} \quad (10)$$

$$= d(i,k)$$

where $x_i$, $y_i$ and $z_i$ are the cartesian coordinates of an imaging point relative to a coordinate system with an arbitrarily located origin, although at one of the detectors of the array 17 (FIG. 1). The term "$\alpha(i,k)$" comprises a scalar value selected to scale d(i,k) to correspond to the geometric spreading loss parameter of the wave 13 (FIG. 1) with a magnitude squared value of "N". Thus, the distance from the ith imaging point to the nth detector located at $x_n$, $y_n$, $z_n$ is given by the following equation:

$$d_i(n) = \sqrt{(x_i - x(n))^2 + (y_i - y(n))^2 + (z_i - z(n))^2} \quad (11)$$

Step 115 computes a conventional image "c" and a minimum variance image "m" according to the respective equations:

$$c = c(x_i,y_i,z_i,k,P) \quad (12)$$

$$= d(x_i,y_i,z_i,k)^H \hat{R}(P,k) d(x_i,y_i,z_i,k)$$

$$m = m(x_i,y_i,z_i,k,P) \quad (13)$$

$$= \frac{1}{d(x_i,y_i,z_i,k)^H \hat{R}(P,k)^{-1} d(x_i,y_i,z_i,k)}$$

for a desired search volume "V" defined by upper and lower values for each of the x, y and z axes. A reporting step 116 enables selective display of these images on a reporting apparatus such as the display terminal 57 (FIG. 3) to provide a graphic representation of the three dimensional images "c" and "m". Preferably step 115 also normalizes the generated display to the peak values of each image.

Referring now to FIG. 4C step 117 enables a user to select a desired imaging point defined as the coordinates ($X_e$, $Y_e$, $Z_e$) and desired frequency band "K". Step 117 also calls the corresponding imaging vector "$d(x_e, y_e, z_e, k)$" from the step 114 for the selected imaging point and the specified frequency bin "k". Step 118 computes space time filter output conventional Fourier coefficients "$y_c(x_e, y_e, z_e, k)$" and minimum variance Fourier coefficients "$y_m(x_e, y_e, z_e, k)$" by the respective equations:

$$y_c(x_e, y_e, z_e, k) = d(x_e, y_e, z_e, k)^H x_i(p,k) \tag{14}$$

and $$y_m(x_e, y_e, z_e, k) = \frac{N(d(x_i,y_i,z_i,k)^H \hat{R}(P,k)^{-1} x(p,k))}{d(x_i,y_i,z_i,k)^H \hat{R}(P,k)^{-1} d(x_i,y_i,z_i,k)} \tag{15}$$

These coefficients correspond to the temporal complex Fourier spectrum of the waveform induced by turbulent blood flow propagated by an energy wave. Step 118 enables the user to then select either of the Fourier coefficients "$y_c$" or "$y_m$" for inverse Fast Fourier Transformation with zero padding and overlap to produce a time sampled turbulent flow wave form time series estimate. Step 120 receives the output of step 118 and performs an autopower spectral analysis of this time series to generate a time integrated spectrum display signal that can be directed from step 120 to a audio report generating step 121 that can be used to generate either aural through such devices as the audio system 67 (FIG. 3) or to the reporting step 116 to employ the reporting sub-module 56 such as the video display terminal 57 (FIG. 3).

The apparatus of this invention thus achieves the objects of this invention and provides an apparatus and method for accurately estimating the location of turbulent flow in a patient's vessels and the wave form propagating from the source. Further, the use of a time-space analysis and an array of detectors enable the extraction of low energy level information in the presence of a high background noise level to enable detection of arterial defects in relatively early stages of a disease or other abnormality than prior methods.

While various changes and modifications to this invention as described will be readily apparent to those skilled in the art, Applicant notes that in areas of a patient having a highly inhomogeneous tissue proximate to the turbulent flow, eigenfiltering provides more robust performance. That is, the selection element 61 can employ the eigenvectors with the largest eigenvalues of $R(P,k)$ determined by the dominant mode element 52 in place of the imaging vectors so that the output of the element 63 enables examination of the dominant mode wave forms. In such case, the element 66 would perform a nonlinear least squares fit of the geometric parameters of the imaging vectors to calculate the eigenvector response over the search volume according to the following:

$$r_e(x_b, z_b, k) = |d(x_b, y_b, k)^H m_e(p,k)|^2 \tag{16}$$

As a further improvement, the scaler factor "e" in equation 8, above, can be set to infinity to provide enhanced resolution of the minimum variance image produced by the element.

The disclosed embodiment provides a generalized processing method and apparatus to account for the interaction of the multiple energy wave fronts and modes thereof that tend to propagate from a turbulent blood flow in the vessel of a patient to an array of sensors. The apparatus and method enables accounting for the various anatomical features, (i.e., organ tissue, muscle tissue, epidermal tissue, skeletal structure and the like) which change the alternation and speed of the force waves generated. Alternatively, a complete model of the volume or region of a patient to be analyzed could be obtained by tomographic or other imaging to define areas of internal inhomogeneous media to thereby generate a full field wave equation based transfer function solution. Alternatively, simple assumptions could be made regarding the location of major inhomogeneities such as the heart, rib bones and the skin layers based on a statistical archival data base.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed is:

1. Apparatus for the diagnosis of pathologic turbulent arterial blood flow in a patient comprising:

wave sensing means positioned at a plurality of spaced sites on the patient for generating a corresponding plurality of space time signals responsive to energy waves propagated from a site of arterial blood flow;

interfacing means responsive to each of the space time signals from said wave sensing means for generating a vectorized data structure corresponding to the energy waves, said interfacing means including a frequency domain transform means for transforming desired portions of said plurality of said space time signals into a continuous sequence of time sampled sensor data; and processing means responsive to the vectorized data structures from said interfacing means for generating a report signal indicating the temporal waveform of the energy wave propagating from the site of turbulent arterial blood flow, the location and spatial configuration of that site.

2. Apparatus as recited in claim 1 wherein said wave sensing means comprises a plurality of discrete auscultatory sensors.

3. Apparatus as recited in claim 2 wherein each of said auscultatory sensors is supported in a predetermined spaced relationship with others of said auscultatory sensors to define an array.

4. Apparatus as recited in claim 3 wherein the predetermined spaced relationship of adjacent ones of said auscultatory sensors is a specific distance that is less than the maximum speed of the wave front in the patient divided by twice the maximum frequency of the space time signals processed by said processing means.

5. Apparatus as recited in claim 1 wherein said interfacing means further comprises means for providing a cardiac timing signal and means for gating the generated plurality of space time signals to produce an array of time sampled data.

6. Apparatus for the diagnosis of pathologic turbulent arterial blood flow in a patient comprising:

wave sensing means positioned at a plurality of spaced sites on the patient for generating a corresponding plurality of space time signals responsive to energy waves propagated from a site of arterial blood flow;

interfacing means responsive to each of the space time signals from said wave sensing means for generating a vectorized data structure corresponding to the energy waves, said interfacing means including:

a means for providing a cardiac timing signal;

a means for gating the generated plurality of space time signals to produce an array of time sampled data; and a Fourier transform means for transforming desired portions of said plurality of said space time signals into a continuous sequence of time sampled sensor data; and processing means responsive to the vectorized data structures from said interfacing means for generating a report signal indicating the temporal waveform of the energy wave propagating from the site of turbulent arterial blood flow, the location and spatial configuration of that site.

7. Apparatus as recited in claim 6 wherein said interfacing means includes means for producing a vectorized data structure in a frequency-time domain.

8. Apparatus as recited in claim 7 wherein said processing means includes means for estimating a cross-spectral density matrix from said vectorized data structure.

9. Apparatus as recited in claim 8 said processing means includes means for computing an eigenstructure from the estimated cross-spectral density to determine dominant modal wave forms.

10. Apparatus as recited in claim 9 wherein said processing means generates an imaging signal from the eigenstructure and an imaging vector for the patient.

11. A method for providing diagnostic information with respect to arterial blood flow in a patient comprising the steps of:

sensing at a plurality of spaced locations on the patient over a time interval, energy waves generated by a turbulent blood flow volume as the energy waves propagate through the patient's tissue, said energy waves producing corresponding signals;

selecting said signals for at least one time interval;

generating vectorized data structures of said signals corresponding to the energy waves sensed at the plurality of locations at the selected time intervals by said sensing step, said generating step including transforming said selected signals to the frequency domain and producing a continuous sequence of time sampled sensor data for use as said vectorized data structure; and processing each of the data structures to produce a reporting signal corresponding to the patient's tissue through which the energy waves pass to the spaced locations to indicate the temporal waveform, location and spatial configuration of the turbulent flow volume.

12. A method as recited in claim 11 wherein said sensing step comprises providing an array of spaced detectors for sensing the energy waves, placing the array on the patient with the detectors at the plurality of locations and generating signals corresponding to the energy waves.

13. A method as recited in claim 11 wherein said generating step comprises temporally gating the signals corresponding to the energy waves sensed at the plurality of locations at the selected time intervals, Fourier transforming the temporally gated signal and arranging the transformed signals in the vectorized data structure.

14. A method as recited in claim 13 wherein said processing step further includes computing a low-rank cross-spectral density matrix and a low-rank cross-spectral density inverse matrix from said vectorized data structure, defining an imaging vector corresponding to the patient's tissue, and determining imaging signals from the imaging vector and the cross-spectral density matrix and its inverse.

15. A method as recited in claim 14 wherein said processing step further includes selecting a spatial imaging point, employing the defined imaging vector for the selected point, inverse Fourier transforming the vectorized data structure including the selected point and spectrum analyzing the inverse Fourier transformed data structure to produce a time domain report signal.

16. A method as recited in claim 11 wherein said processing step further includes computing a low-rank cross-spectral density matrix and a low-rank cross-spectral density inverse matrix from said vectorized data structure, defining an imaging vector corresponding to the patient's tissue, and determining imaging signals from the imaging vector and the cross-spectral density matrix and its inverse.

17. A method as recited in claim 16 wherein said processing step further includes selecting a spatial imaging point, employing the defined imaging vector for the selected point, inverse Fourier transforming the vectorized data structure including the selected point and spectrum analyzing the inversely transformed data structure to produce a report signal.

18. A method as recited in claim 16 wherein said processing step further includes selecting a spatial imaging volume, employing the defined imaging vectors for the selected volume, inverse Fourier transforming the vectorized data structure including the selected volume, and spectrum analyzing the inversely transformed data structure to produce a report signal.

19. A method for providing diagnostic information with respect to arterial blood flow in a patient comprising the steps of:

sensing at a plurality of spaced locations on the patient over a time interval, energy waves generated by a turbulent blood flow volume as the energy waves propagate through the patient's tissue said energy waves producing corresponding signals;

selecting said signals for at least one time interval;

generating vectorized data structures of said signals corresponding to the energy waves sensed at the plurality of locations at the selected time intervals by said sensing step, said generating step comprising temporally gating the signals corresponding to the energy waves sensed at the plurality of locations at the selected time intervals, Fourier transforming the temporally gated signal and arranging the transformed signals in the vectorized data structure; and processing each of the data structures to produce a reporting signal corresponding to the patient's tissue through which the energy waves pass to the spaced locations to indicate the temporal waveform, location and spatial configuration of the turbulent flow volume.

20. A method as recited in claim 19 wherein said processing step further includes computing a low-rank cross-spectral density matrix and a low-rank cross-spectral density inverse matrix from said vectorized data structure, defining an imaging vector corresponding to the patient's tissue, and determining imaging signals from the imaging vector and the cross-spectral density matrix and its inverse.

21. A method as recited in claim 20 wherein said processing step further includes selecting a spatial imaging point, employing the defined imaging vector for the selected point, inverse Fourier transforming the vectorized data structure including the selected point, and spectrum analyzing the inverse Fourier transformed data structure to produce a time domain report signal.

\* \* \* \* \*